United States Patent
VanEperen et al.

(10) Patent No.: US 6,589,149 B1
(45) Date of Patent: Jul. 8, 2003

(54) METHOD AND APPARATUS FOR APPLYING A CURVED COMPONENT TO A MOVING WEB

(75) Inventors: David James VanEperen, Appleton, WI (US); Adam Lewis Daniels, Menasha, WI (US); Kevin Lester Fiedler, Appleton, WI (US); Gene Mark Gregory, Neenah, WI (US); Steven Michael Parsons, Neenah, WI (US); James Bennington Stopher, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 355 days.

(21) Appl. No.: 09/638,781

(22) Filed: Aug. 15, 2000

(51) Int. Cl.$^7$ .............................................. B31B 49/00
(52) U.S. Cl. ....................... 493/380; 156/163; 156/229; 156/494
(58) Field of Search ................................. 493/380, 381, 493/382; 156/163, 164, 229, 494–496

(56) References Cited

U.S. PATENT DOCUMENTS

| | | | | |
|---|---|---|---|---|
| 4,293,367 A | * | 10/1981 | Klasek et al. | 156/164 |
| 4,486,192 A | * | 12/1984 | Sigl | 604/366 |
| 4,704,116 A | | 11/1987 | Enloe | |
| 4,801,345 A | * | 1/1989 | Dussaud et al. | 156/164 |
| 4,915,767 A | * | 4/1990 | Rajala et al. | 156/161 |
| 4,917,746 A | * | 4/1990 | Kons et al. | 156/164 |
| 5,275,676 A | | 1/1994 | Rooyakkers et al. | |
| 5,525,175 A | * | 6/1996 | Blenke et al. | 156/161 |
| 5,582,668 A | * | 12/1996 | Kling | 156/160 |
| 5,584,954 A | * | 12/1996 | van der Klugt | 156/163 |
| 5,660,664 A | * | 8/1997 | Herrmann | 156/161 |
| 5,683,531 A | * | 11/1997 | Roessler et al. | 156/163 |
| 5,779,689 A | * | 7/1998 | Pfeifer et al. | 156/41 |
| 5,904,675 A | | 5/1999 | Laux et al. | |
| 5,993,433 A | | 11/1999 | St. Louis et al. | |
| 6,284,081 B1 | * | 9/2001 | Vogt et al. | 156/161 |
| 6,287,409 B1 | * | 9/2001 | Stephany | 156/161 |

FOREIGN PATENT DOCUMENTS

WO    WO 01/45611 A1    6/2001

\* cited by examiner

Primary Examiner—John Sipos
Assistant Examiner—Hemant M Desai
(74) Attorney, Agent, or Firm—Paul Yee; Thomas M. Parker

(57) ABSTRACT

The present invention provides a process and apparatus for applying a web component (42) to a moving substrate (44). The process aspect includes a delivering of the web component (42) to a rotatable applicator wheel (58). The applicator wheel has an entry surface-region (114), an exit surface-region (116), a transport surface-region (118), and an applicator wheel diameter (112). The web component (42) is contacted onto the entry surface-region (114) of the applicator wheel (58), and the applicator wheel is rotated to move the web component along a substantially circumferential, applicator path along the transport surface-region (118) of the applicator wheel. The applicator wheel (58) is oscillated about a pivot axis (102) which is spaced from the moving substrate (44) by a pivot distance (100), and the web component (42) is operatively applied from the exit surface-region (116) of the applicator wheel (58) onto the moving substrate (44) to provide a desired curved web configuration. In a particular aspect, the applicator wheel diameter (112) can be at least a selected percentage of the pivot distance (100).

28 Claims, 11 Drawing Sheets

METHOD AND APPARATUS FOR APPLYING A CURVED COMPONENT TO A MOVING WEB

FIELD OF THE INVENTION

The present invention relates to a method and apparatus for applying a web component in a curved configuration onto a moving substrate web. More particularly, the present invention relates to a method and apparatus for applying web components in a curved configuration at each of the leg opening regions of a disposable absorbent article, such as a disposable diaper.

BACKGROUND OF THE INVENTION

Limited use absorbent articles, such as disposable diapers, have incorporated elasticized gathers at the leg openings of the article. The leg openings are positioned at the lateral side margins of the article, and can be elasticized with a single web component or with multiple web components.

Various techniques have been developed for applying multiple elastic strands onto a substrate. It has been desirable to employ curved web components which better follow the contours of the leg openings formed in the side margins of disposable absorbent garments. For example, prior techniques have been employed to apply one or more elastomeric strands in a curved pattern along the length of a moving substrate. Prior techniques have also been employed to apply a curved elastomeric composite web along the length of a moving substrate.

Conventional techniques, such as those described above, have not provided an adequate system for efficiently placing a relatively wide web component, such as a wide elastic composite member, across a desired curvilinear location on the surface of a moving substrate. Such conventional techniques have not been able to provide desired amounts of curvature, and have generated excessive distortions in the web component. In addition, the conventional techniques have not been sufficiently adaptable to accommodate web components of different sizes.

BRIEF DESCRIPTION OF THE INVENTION

Generally stated, the present invention provides a distinctive process and apparatus for applying a web component to a moving substrate. The technique of the invention includes a delivering of the web component to an applicator wheel. The applicator wheel has an entry surface-region, an exit surface-region, a transport surface-region, and an applicator wheel diameter. The web component is contacted onto the entry surface-region of the applicator wheel, and the web component is moved along a substantially circumferential, applicator path along the transport surface-region of the applicator wheel. The applicator wheel is oscillated about a pivot axis which is spaced from the moving substrate by a pivot distance, and the web component is applied from the exit surface-region of the applicator wheel onto the moving substrate to provide a curved web configuration.

In a particular aspect, the applicator wheel diameter can be at least a minimum, selected percentage of the pivot distance. Another aspect of the present invention can include a selective adjusting of an exit-span distance between the applicator wheel and an integration roll. A further aspect can include an urging of the component web against the moving substrate at a selected point that is located relatively downstream from a contact point at which the web component is applied to the moving substrate.

In its various aspects, the present invention can more effectively and efficiently assemble a relatively wide web component, such as a wide elastomeric composite member, along a desired curvilinear location on the surface of a moving substrate. The technique of the invention can provide larger amounts of curvature, and can reduce the generation of excessive distortions in the assembled web component. In addition, the technique of the invention can be readily adjusted to accommodate web components having different sizes.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The various embodiments of the invention will be described in the context of producing a disposable absorbent article, such as a disposable diaper. It is, however, readily apparent that the present invention may also be employed to produce other articles, such as adult incontinence products, feminine care products, child-care training pants, covers, capes, gowns, garment pants and the like.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

Figure 1:
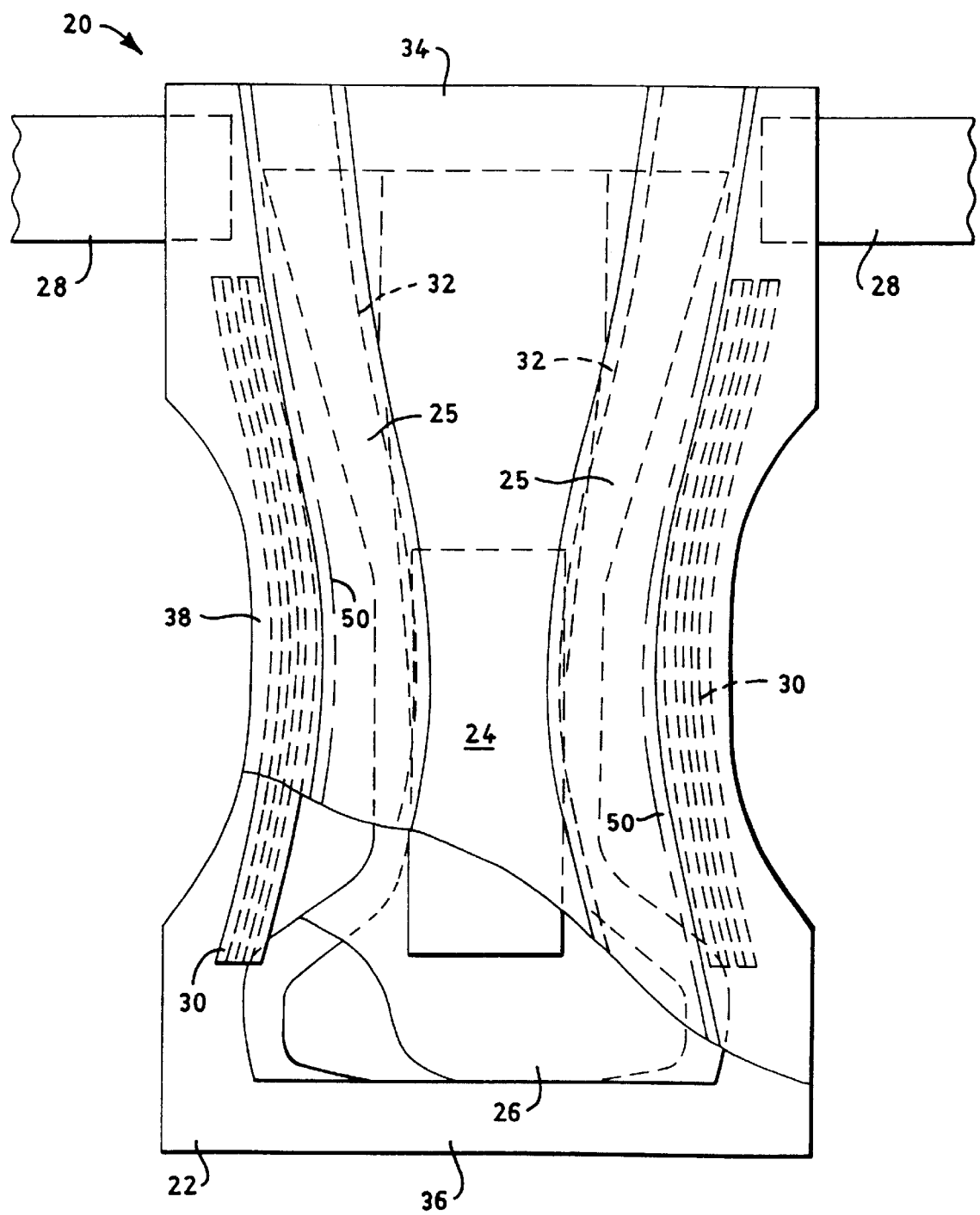
FIG. 1 representatively shows a partially cut away, plan view of a diaper article which incorporates a complementary pair of curved members.

Disposable articles are typically intended for limited use, and are not intended to be laundered or otherwise cleaned for reuse. For example, a disposable diaper is discarded after it has become soiled by the wearer. With reference to FIG. 1, a representative disposable diaper article is shown in a fully-extended condition with all of its elasticized gathers removed. The garment article represented by disposable diaper 20 has a first waistband section 34, a second waistband section 36, and an intermediate section 38 which interconnects the waistband sections. The diaper comprises a backsheet layer 22, a liquid-permeable topsheet layer 24 superposed in facing relation with the backsheet layer, and an absorbent body 26 interposed between the backsheet and topsheet layers.

At least one fastening member 28, and preferably a complementary, opposing pair thereof, are connected to the first waistband section 34 of the diaper 20. In the illustrated embodiment, the fastener 28 is composed of an adhesive tape fastener. Optionally, interengaging mechanical fasteners, such as hook-and-loop fasteners, snaps, hooks, buckles and the like, may be employed. The fasteners are typically used to secure the diaper about the waist of the wearer, and leg elastic members 30 are typically disposed along the side margins of the article.

To further improve the article, the process and apparatus of the invention can efficiently produce a curved web component, such as the representatively shown curved containment flap member 25, which is operatively assembled into the article. In desired arrangements, the technique of the invention can provide an article having a complementary pair of the curved containment flaps, and the containment flaps may be elasticized, such as by incorporating elastic members 32. Examples of a representative article having curved containment flap components are disclosed in U.S. Pat. No. 4,704,116 entitled DIAPERS WITH ELASTICIZED SIDE POCKET by K. M. Enloe which was issued Nov. 11, 1987, the entire disclosure of which is hereby incorporated by reference in manner that it is consistent (not in contradiction) herewith.

Figure 1A:
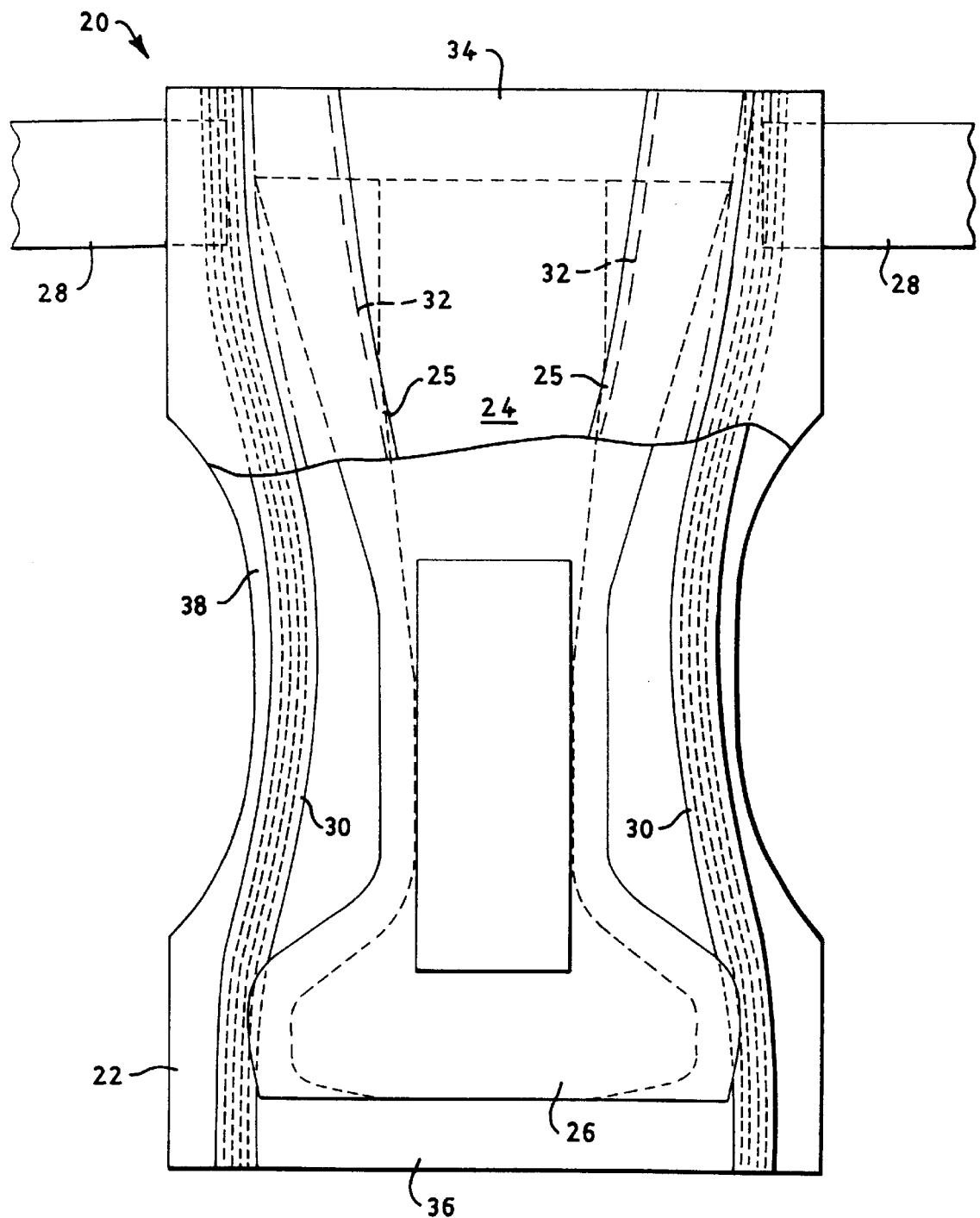
FIG. 1A representatively shows a plan view of a diaper article which incorporates a complementary pair of curved leg elastic members for elasticizing the leg openings at the side margins of the article.
Figure 1B:
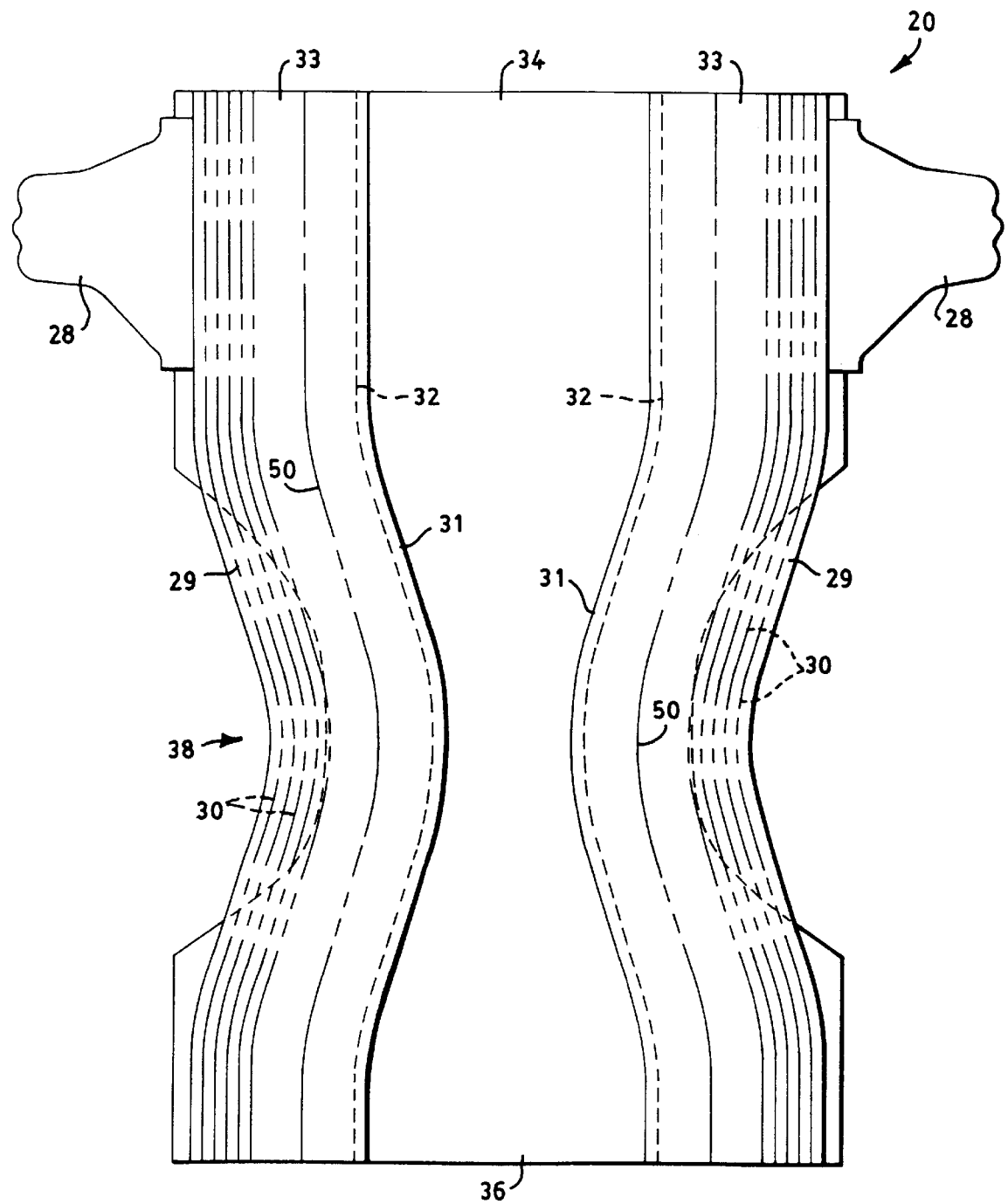
FIG. 1B representatively shows a plan view of a diaper article which incorporates a complementary pair of curved gusset-flap members.

Still other arrangements of the invention can, for example, provide an article having a curved web component in the form of a curved leg gusset member or a curved leg elastic member 30, as representatively shown in FIG. 1A. In further examples, the invention can provide a curved web component in the form of a composite gusset-flap member 33 having a leg gusset section 29 and a containment flap section 31, as representatively shown in FIG. 1B. Additional details of a representative article having the leg gusset component are disclosed in U.S. Pat. No. 5,904,675 entitled AN ABSORBENT ARTICLE WITH IMPROVED ELASTIC MARGINS AND CONTAINMENT SYSTEM by D. R. LAUX et al. which was issued May 18, 1999, the entire disclosure of which is hereby incorporated by reference in manner that it is consistent herewith. Details of a representative article having the gusset-flap component are disclosed in U.S. Pat. No. 5,993,433 entitled ABSORBENT ARTICLE WITH ENHANCED ELASTIC DESIGN FOR IMPROVED AESTHETICS AND CONTAINMENT by R. G. St. Louis et al. which was issued Nov. 30, 1999, the entire disclosure of which is hereby incorporated by reference in manner that it is consistent herewith.

Figure 2:
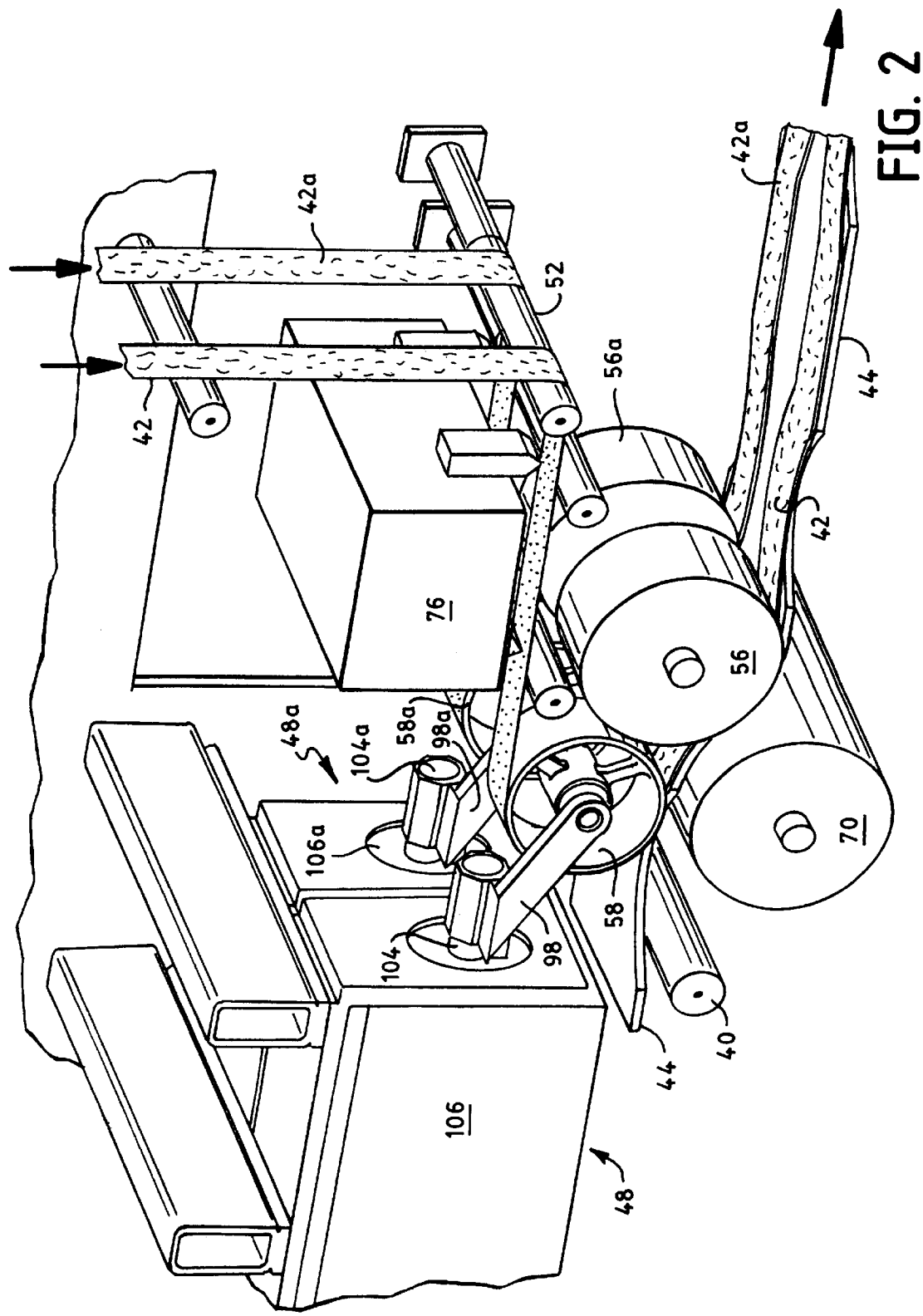
FIG. 2 representatively shows an isometric, perspective view an apparatus for applying a plurality of web components in individual, complementary, curved patterns along the length of a moving substrate web.
Figure 3:
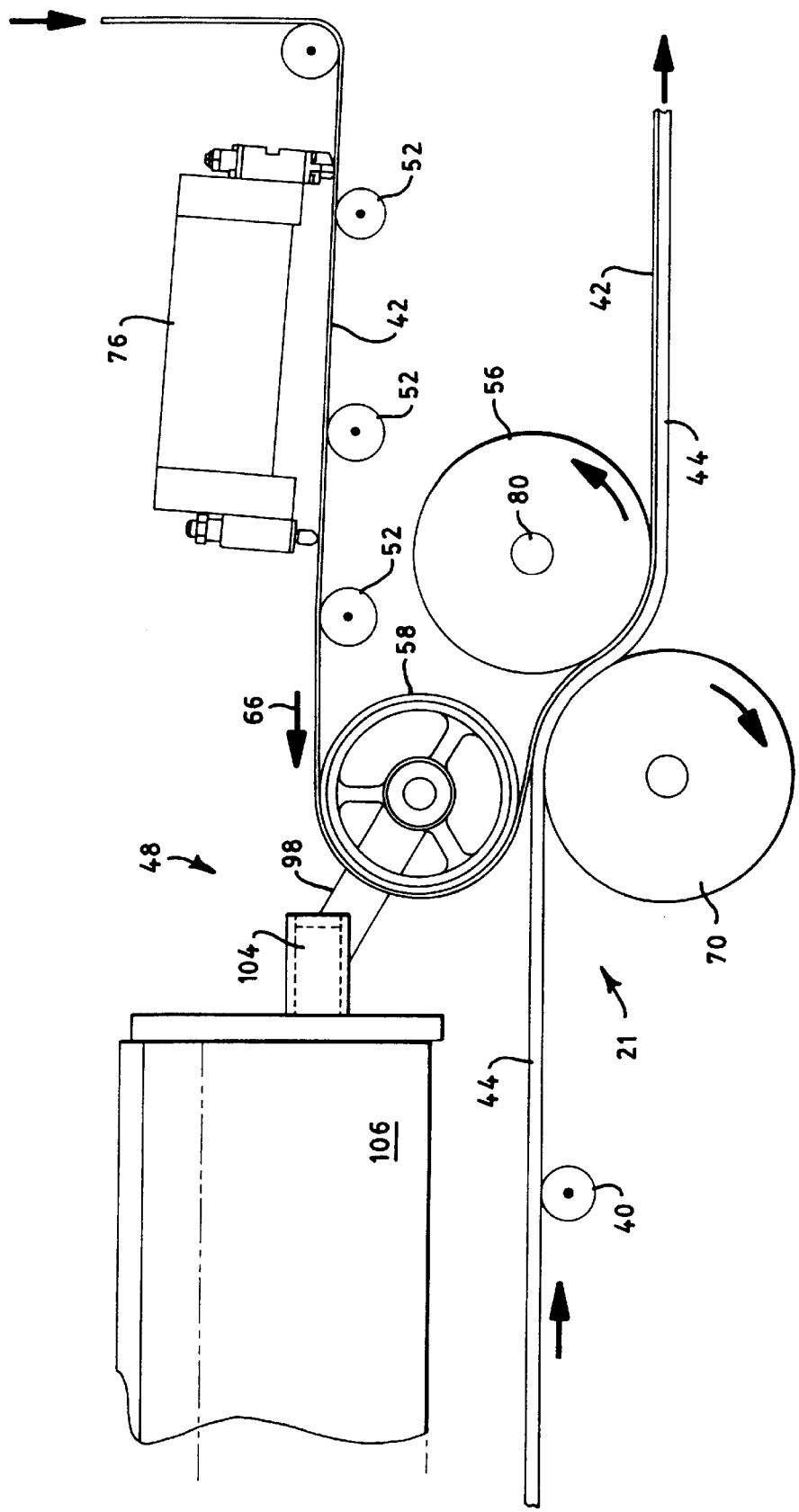
FIG. 3 representatively shows a schematic, side elevational view of a process and apparatus for applying at least one web component in a curved pattern along the surface of a moving substrate web.
Figure 4:
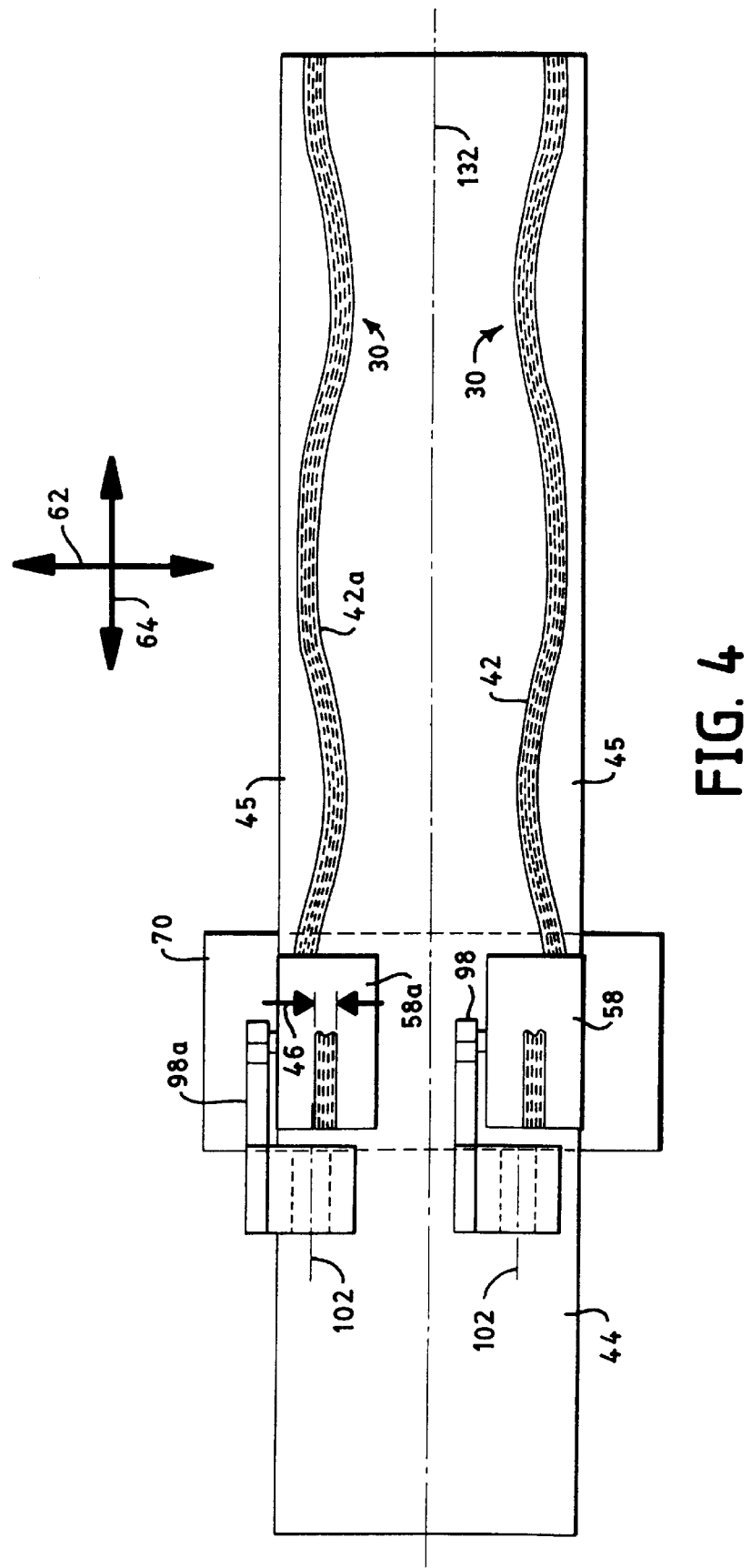
FIG. 4 representatively shows a schematic, top plan view of a portion of a process and apparatus for applying a web component, such as a leg gusset member or leg elastic member, along a curvilinear location that extends across the surface of a moving substrate.

With reference to FIGS. 2, 3 and 4, the process and apparatus 21 of the invention can have an appointed machine-direction 64 and an appointed cross-direction 62. For the purposes of the present disclosure, the machine-direction 64 is the direction along which a particular component or material is transported length-wise along and through a particular, local position of the apparatus and method of the invention. The cross-direction 62 lies generally within the plane of the material being transported through the process and is aligned perpendicular to the local machine-direction 64. Accordingly, in the view of the arrangement representatively shown in FIG. 3, the cross-direction 62 extends perpendicular to the plane of the sheet of the drawing.

FIGS. 2, 3, 3A and 6 generally show a process and apparatus 21 for assembling or otherwise applying a web component 42 to a moving substrate web 44 along a selected curvilinear location on the substrate web. As representatively shown, a process aspect of the invention can include a delivering of the web component 42 to an applicator wheel 58. The applicator wheel has an entry surface-region 114, an exit surface-region 116, a transport surface-region 118, and an applicator wheel diameter 112. The web component 42 is contacted onto the entry surface-region 114 of the applicator wheel 58, and the web component is moved along a substantially circumferential, applicator path 120 on the transport surface-region 118 of the applicator wheel. In desired configurations, the applicator wheel is rotated to move the web component along the substantially circumferential, applicator path on the transport surface-region 118 of the applicator wheel. The applicator wheel 58 is oscillated about a pivot axis 102 which is spaced from the moving substrate 44 by a selected pivot distance 100, and the web component 42 is applied from the exit surface-region 116 of the applicator wheel 58 onto the moving substrate 44 to provide a curved web configuration.

An apparatus aspect of the invention includes a rotatable applicator wheel 58 having an entry surface-region 114, an exit surface-region 116, a transport surface-region 118 and an applicator wheel diameter 112. The applicator wheel 58 is configured to move the web component 42 along a substantially circumferential applicator path with the transport surface-region 118 of the applicator wheel. A web conveyor 52 delivers the web component 42 to the applicator wheel 58 and contacts the web component 42 onto the entry surface-region 114 of the applicator wheel. A pivot drive mechanism 106 oscillates the applicator wheel 58 about a pivot axis 102 to direct the web component 42 from the exit surface-region 116 of the applicator wheel onto the moving substrate 44 in a curved web configuration. The pivot axis 102 is spaced from the moving substrate 44 by a selected pivot distance 100.

In particular aspects, the applicator wheel diameter 112 can be at least a selected size or at least a selected percentage of the pivot distance 100. A desired aspect of the invention can provide an applicator wheel diameter 112 which is substantially equal to the pivot distance 100. Further aspects of the technique of the invention can include a securing of the web component 42 to the moving substrate 44 with a curved attachment 50 (e.g. FIG. 4A). For example, the technique of the invention can include a depositing of an adhesive onto the web component 42 prior to the contacting of the web component onto the entry surface-region 114 of the applicator wheel 58.

Another aspect of the invention can include a pressing of the web component 42 onto the moving substrate 44. For example, the technique of the invention can include a positioning of an integration roll 70 at a location which is operatively adjacent the applicator wheel 58. A pressing nip roll 56 can be positioned relatively downstream from the applicator wheel 58, and the moving substrate 44 can be directed with the integration roll 70 into an operative contact with the web component 42. The web component 42 can be urged against the moving substrate 44 in a nip which is formed between the integration roll 70 and the pressing nip roll 56. Additionally, the moving substrate 44 and the web component 42 can be wrapped around the integration roll 70 along a wrap length 72 which is at least a selected portion or percentage of a total circumference of the integration roll 70. In desired arrangements, the wrapping of the moving substrate 44 and the web component 42 around the integration roll 70 can be conducted by employing the pressing nip roll 56.

The various aspects of the present invention, alone and in combination, can advantageously assemble a web component, such as an elastomeric composite member, along a desired curvilinear location on the surface of a moving substrate with greater effectiveness and efficiency. The method and apparatus of the invention can advantageously accommodate relatively wide web components. In addition, the technique of the invention can provide larger amounts of curvature, and can reduce the generation of excessive distortions in the assembled web component.

The technique of the invention can also be readily adjusted to better match the arrangement of the process and apparatus to the particular size of the web component being processed. As a result, the distinctive configurations of the invention can produce a larger amount of curvature in the web component 42, and is less likely to produce undesired wrinkles or C-folds in the web component during the curving operation.

To produce the desired curved configuration of the web component 42 on the moving substrate 44, the invention advantageously incorporates a distinctive, curved-component processing system which can integrate the web component 42 onto the moving substrate 44 along the desired curvilinear location. In the representatively shown configuration, a conventional transporting mechanism, such as provided by the illustrated system of transport rollers 40, operatively delivers the substrate 44 to the processing system along the appointed machine-direction. The substrate 44 is desirably substantially continuous along the machine-direction, and may, for example, be a web composed of a single material. Alternatively, the substrate 44 may be a composite web composed of a plurality of two or more components composed of different materials or composed of the substantially the same material.

A suitable transport or supply system, such as a mechanism provided by a system of conveying rollers 52, delivers the web component 42 to the applicator wheel 58. The web component 42 desirably extends substantially continuously along the machine-direction, and may, for example, be a unitary member composed of a single material. Alternatively, the web component 42 may be a composite member having a plurality of individual components. The composite web component may, for example, include a combination of elastomeric and non-elastomeric components, and the individual elastomeric components may be composed of the same elastomeric material or different elastomeric materials.

Where the web component 42 is elastomeric, desired levels of tension and stretch can be applied to the web component 42 prior to its delivery onto the applicator wheel 58. The stretch and tension can be applied using conventional techniques well known in the art. For example, the web component 42 can be stretched about 200–400 percent employing a conventional system of differential traction rolls operated at different rotational speeds.

It has been found that the technique of the invention can be particularly advantageous when it is configured to process a relatively wide web component 42. In such configurations, the web component 42 can be configured to have a cross-directional width 46 (e.g. FIG. 4) which is at least a minimum of about 1 cm. The cross-directional width of the web can alternatively be at least about 2 cm to provide improved performance. In other aspects, the cross-directional width of the web can be up to a maximum of about 8 cm or more, and alternatively, can be up to about 4.5 cm.

For the purposes of the present disclosure, it should be readily appreciated that various conventional transport mechanisms or supply mechanisms may be employed to move the various components or assemblies through the process and apparatus. Such mechanisms can, for example, include rollers, slides, conveyor belts, conveyor chains, mechanical suspension systems, fluid suspension systems, electro-magnetic suspension systems, and the like, as well as combinations thereof. The transport devices can be driven by any conventional power source, such as engine power, electrical power, magnetic power, water power or the like, as well as combinations thereof.

In the present disclosure, the various aspects of the invention may be described with respect to an individual processing unit 48. It should be understood, however, that particular embodiments of the invention may comprise multiple processing units that are appropriately coordinated with one another to provide desired arrangements of multiple curved web components on the selected substrate 44. Each of the multiple processing units can be configured in accordance with the aspects of the invention that are described with respect to a single processing unit 48.

For example, when constructing a garment article, such as a disposable diaper, it may be desirable to apply one or more appointed web components onto each of a laterally opposed pair of substrate side portions 45 (e.g. FIG. 4). As illustrated in FIG. 2, the invention can readily be configured to locate a designated processing unit or system 48 or 48a in a corresponding association with each of the side regions 45 to provide a corresponding curved web component 42 or 42a that is operatively secured to the substrate 44. Each processing unit includes a corresponding set of the processing components that is described in the context of a single processing unit. In particular arrangements, each processing unit may have an individual, designated processing component. For example, each processing unit can include a designated applicator wheel 58 or 58a which applies its corresponding web component 42 or 42a onto the substrate 44 along its designated curvilinear location (e.g. FIG. 4). Alternatively, the various processing units may share a processing component, such as the integration roll 70.

Figure 4A:
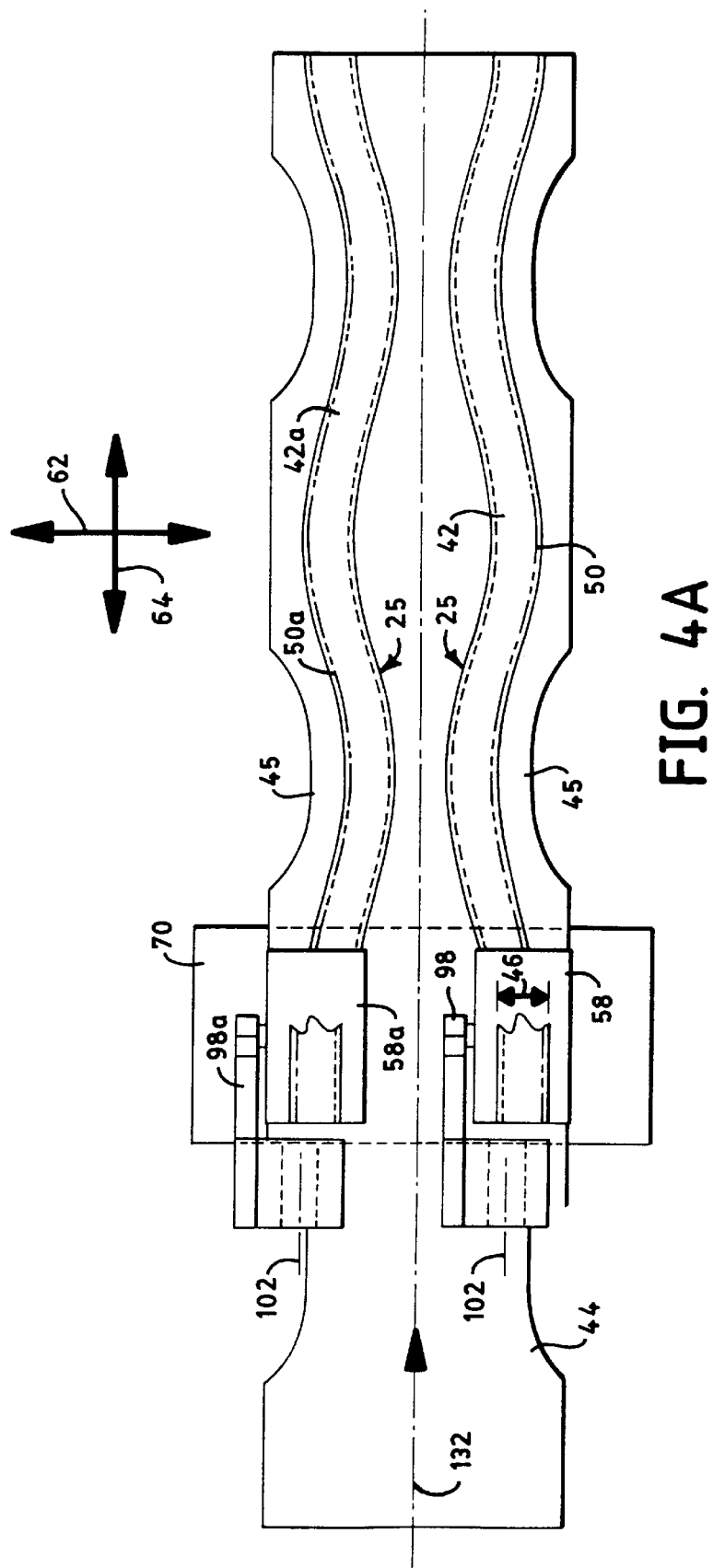
FIG. 4A representatively shows a schematic, top plan view of a portion of a process and apparatus for applying another web component, such as a containment flap member, along a curvilinear location extending across the surface of a moving substrate.

Each applicator wheel can be configured to selectively change a lateral positioning of its corresponding web component relative to the cross-direction 62. Accordingly each web component can have the same curved configuration or a different curved configuration, as desired. With reference to FIG. 4A, the individual curvilinear locations and arrangements of the corresponding web components 42 and 42a can be positioned in each of the two side regions 45 of the substrate 44, and can be substantially symmetrically disposed relative to a longitudinal centerline 132 of substrate 44. Additionally, the configuration of curvilinear arrangement and location of the web component 42 can be approximately a mirror image of the oppositely positioned, curvilinear arrangement and location of the web component 42a. Similarly, the configuration of the curvilinear attachment 50 of the web component 42 can be approximately a mirror image of the oppositely positioned, curvilinear attachment 50a of the web component 42a.

Figure 4B:
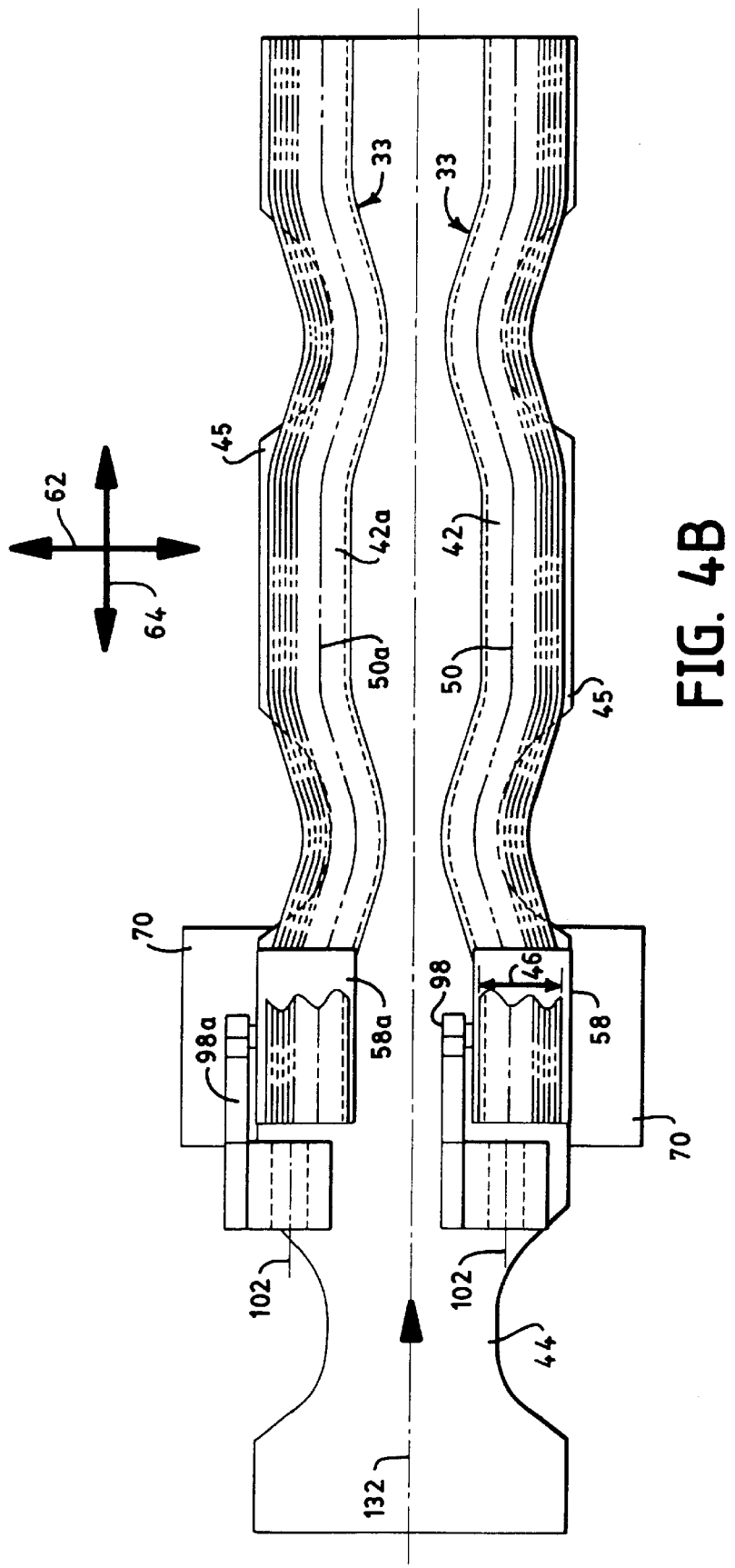
FIG. 4B representatively shows a schematic, top plan view of a portion of a process and apparatus for applying still another web component, such as a combination gusset-flap member, along a curvilinear location extending across the surface of a moving substrate.

Various techniques may be employed to help secure web the component 42 onto the moving substrate 44. For example, desired securements may be provided by adhesive bonding, thermal bonding, ultrasonic bonding or the like, as well as combinations thereof. With reference again to FIGS. 2 and 3, a bonding mechanism, such as provided by the shown adhesive applicator 76, can provide a selected attachment 50 between the web component 42 and the substrate 44. For example, a distribution of adhesive in a selected arrangement can operatively secure the web component 42 to the substrate 44 along the desired curvilinear location. The bonding mechanism is desirably configured to substantially avoid contacting the adhesive with the attachment wheel 58, and is desirably positioned relatively upstream from the applicator wheel. Accordingly, the adhesive can be applied to an appointed region of the web component 42 prior to contacting the web component on the applicator wheel. For example, particular arrangements of the invention can apply the adhesive along substantially the entire width of the web component (e.g. FIG. 4), and other arrangements can apply the adhesive along an appointed outboard edge region of the web component (e.g. FIG. 4A). Further arrangements can apply the adhesive along an appointed middle region of the web component (e.g. FIG. 4B). Still other arrangements can apply the adhesive along an appointed inboard edge region of the web component. For example, where the web component 42 includes only a leg gusset portion 29, the attachment 50 can be located along the inboard edge region of the leg gusset. In the representatively shown arrangements, the distributed adhesive can provide a curvilinear attachment 50 between the curved web component 42 and the substrate 44. The curvature of the attachment 50 may or may not substantially match the curvature of the web component 42. Optionally, the distribution of the adhesive on the web component may be coordinated with the curving operation to provide a generally linear attachment, as viewed on final assembly composed of the web component 42 and the substrate 44.

The web component 42 can, for example, be adhered to the substrate 44 with a hot melt, pressure sensitive adhesive, such as a 2525A adhesive available from ATO Findley, a business having offices located in Wauwatosa, Wis. The selected hot melt adhesive is deposited onto the web component 42 in a selected pattern, such as a generally continuous bead, a generally continuous slot coating pattern, an intermittent slot coating pattern, a meltblown pattern, a continuous or discontinuous swirl pattern, a continuous or discontinuous oscillating pattern, or the like, as well as combinations thereof. In the shown configuration, for example, the applicator 76 can be configured to deposit a continuous bead and an intermittent slot-coat pattern of hot melt adhesive onto the moving web component 42.

Figure 3A:
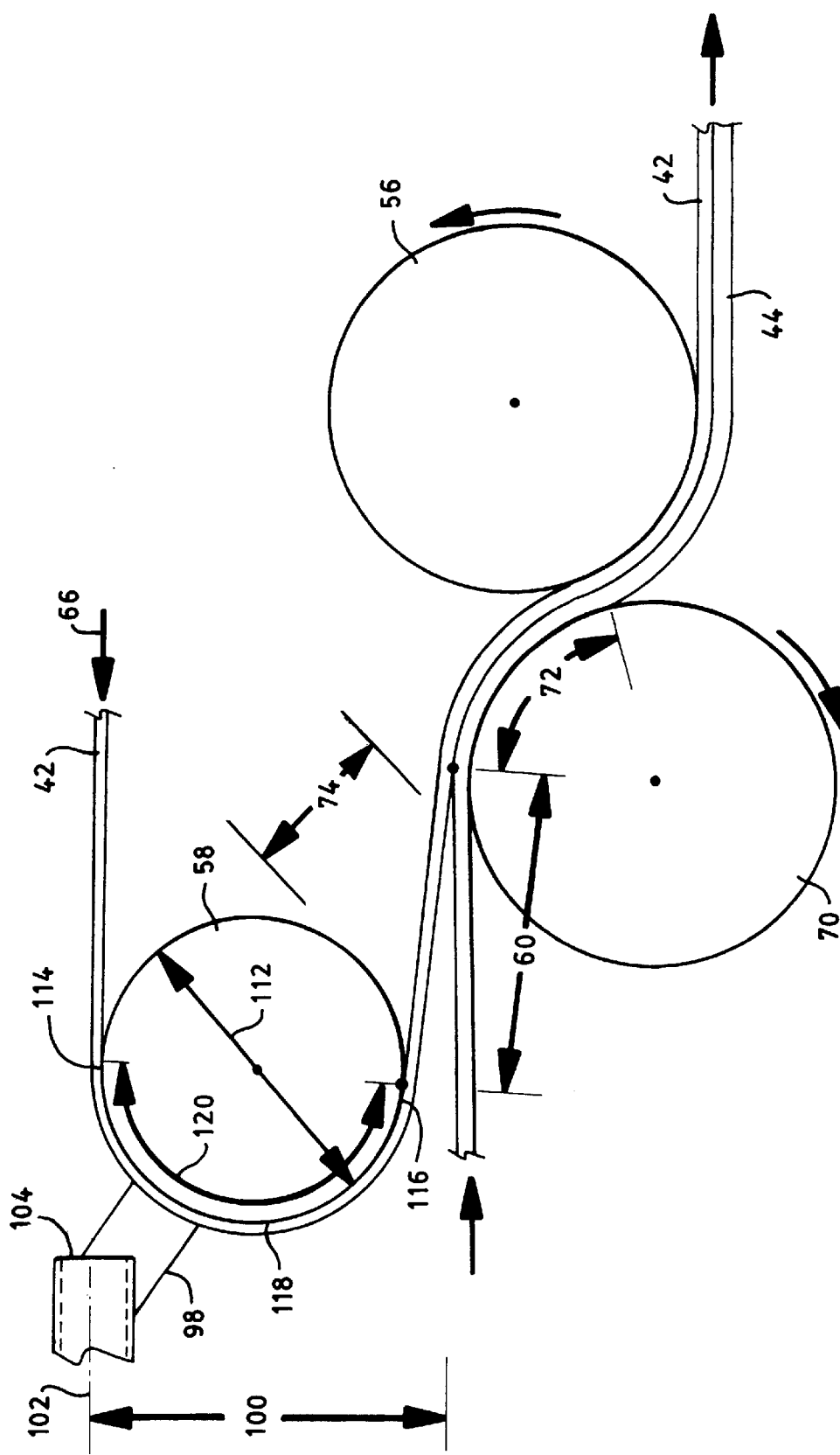
FIG. 3A representatively shows a schematic, side elevational view of a portion of the process and apparatus illustrated in FIG. 3.

With reference to FIGS. 2 through 3A, the technique of the invention can further include an aligning of the pivot axis 102 substantially along a local machine-direction 64 of the moving substrate 44 at the location of the applicator wheel 58. In a particular aspect, the delivering of the web component 42 can be configured to move the web component along an entry path 66 which is substantially aligned and co-linear with the pivot axis 102. The applicator wheel 58 has a wheel diameter 112, and an axial length 110 (e.g. FIG. 5). A pivot arm 98 connects the applicator wheel 58 to a pivot shaft 104, and the pivot arm is operatively attached to the pivot shaft. The pivot shaft is rotatable about a pivot axis 102, and the pivot axis is spaced away from the substrate 44 by a pivot distance 100. The pivot distance 100 is measured between the pivot axis 102 and an assembly point at the integration roll 70 where the process joins the web component 42 to the moving substrate 44, and is measured along a line that is perpendicular to the pivot axis and extends to substantially intersect the assembly point at the integration roll. A pivot drive mechanism is operatively connected to twist the pivot shaft in the desired oscillating motion.

In particular aspects, the applicator wheel diameter 112 can be at least a minimum of about 2.5 cm. The applicator wheel diameter can alternatively be at least about 7 cm, and optionally, can be at least about 11 cm to provide improved performance. In other aspects, the applicator wheel diameter can be not more than a maximum of about 25 cm. The applicator wheel diameter can alternatively be not more than about 20 cm, and optionally, can be not more than about 15 cm to provide improved effectiveness.

In other aspects, the applicator wheel diameter 112 can be at least a minimum of about 50% of the pivot distance 100. The applicator wheel diameter can alternatively be at least about 75%, and optionally, can be at least about 90% of the pivot distance to provide improved performance. In other aspects, the applicator wheel diameter can be not more than a maximum of about 150% of the pivot distance. The applicator wheel diameter can alternatively be not more than about 120%, and optionally, can be not more than about 110% of the pivot distance to provide improved effectiveness.

If the diameter of the applicator wheel is too low, the applicator wheel will need to be pivoted and swung through an excessively large arc to generate the desired amount of curvature in the applied location of the web component 42. Additionally, there can be an insufficient area amount of contact between the web component and the outer surface of the applicator wheel, and an excessive tendency to form wrinkles in the web component during the curving operation. If the applicator wheel diameter is too large, the inertia of the applicator wheel can be excessive, and undesirably large amounts of force and energy may be needed to generate the appointed amounts of pivoting and oscillating movement.

The length of the applicator wheel along the cross-direction 62 can advantageously be configured to accommodate relatively wide web components. For example, the applicator wheel 58 can have an axial length 110 which is at least a minimum of about 3 cm. The axial length of the applicator wheel can alternatively be at least about 3.7 cm, and optionally, can be at least about 4.5 cm to provide improved performance. In other aspects, the axial length can be not more than a maximum of about 13 cm. The axial length of the applicator wheel can alternatively be not more than about 10 cm to provide improved effectiveness.

The applicator wheel may be substantially non-rotatable. Desirably, the applicator wheel 58 is rotatable, and the rotating of the applicator wheel 58 can operatively move the web component 42 from the entry surface-region 114 to the exit surface-region 116 of the applicator wheel. As representatively shown, such movement can operatively occur on or along the transport surface-region 118 of the applicator wheel 58. In particular aspects, rotating of the applicator wheel 58 can move the web component 42 along a transport surface-region 118 which extends along at least about 37% of a peripheral, outer circumference of the applicator wheel 58, and optionally, can extend along approximately 62%, or more, of the outer circumference of the applicator wheel. The transport surface-region can alternatively extend along approximately 50% of the outer circumference of the applicator wheel to provide improved performance.

If the extent of the transport surface-region 118 is too low, the applicator wheel will need to be pivoted and swung through an excessively large arc to generate the desired amount of curvature in the applied location of the web component 42. Additionally, there can be an excessive tendency to form wrinkles in the web component during the curving operation. If the extent of the transport surface-region is too large, the system may generate an excessive weaving motion in the web component 42.

The substantially continuous contact of the web component 42 along the transport surface-region 118 of the relatively large diameter applicator wheel can provide less slippage and less "walking" of the component web across the roll surface during the curving process. As a result, there can be a closer correspondence between the amount of cross-directional displacement of the exit surface-region 116 of the applicator wheel and the cross-directional displacement of the web component 42 in its final curved configuration when attached to the substrate web 44. Less over travel of the exit surface-region along the cross-direction 62 is required to generate the desired amount of curvature within the applied web component 42.

The configuration of the relatively large applicator wheel 58 can produce less wrinkling and less c-folding of the component web 42 during the curving process. Due to the relatively large diameter 112 of the applicator wheel 58, the desired amount of curvature in the web component 42 can be generated with a relatively smaller rocking or pivot angle 108 (e.g. FIG. 5). If the diameter of the applicator wheel is excessively large, the technique may exceed available space limitations, and the rotational inertia of the applicator wheel can inhibit the desired rocking motion of the applicator wheel. Excessively expensive or complicated pivot drive mechanisms may be needed to generate the rapid changes in speed and direction of the rocking motion desired in the pivoting applicator wheel during its oscillation.

In the shown configuration, the applicator wheel 58 has a substantially cylindrical peripheral outer surface. In alternative configurations, the outer peripheral surface of the applicator wheel can be selectively contoured, as desired. For example, the applicator wheel may have a convex contour or concave contour with respect to its axial length dimension.

Figure 5:
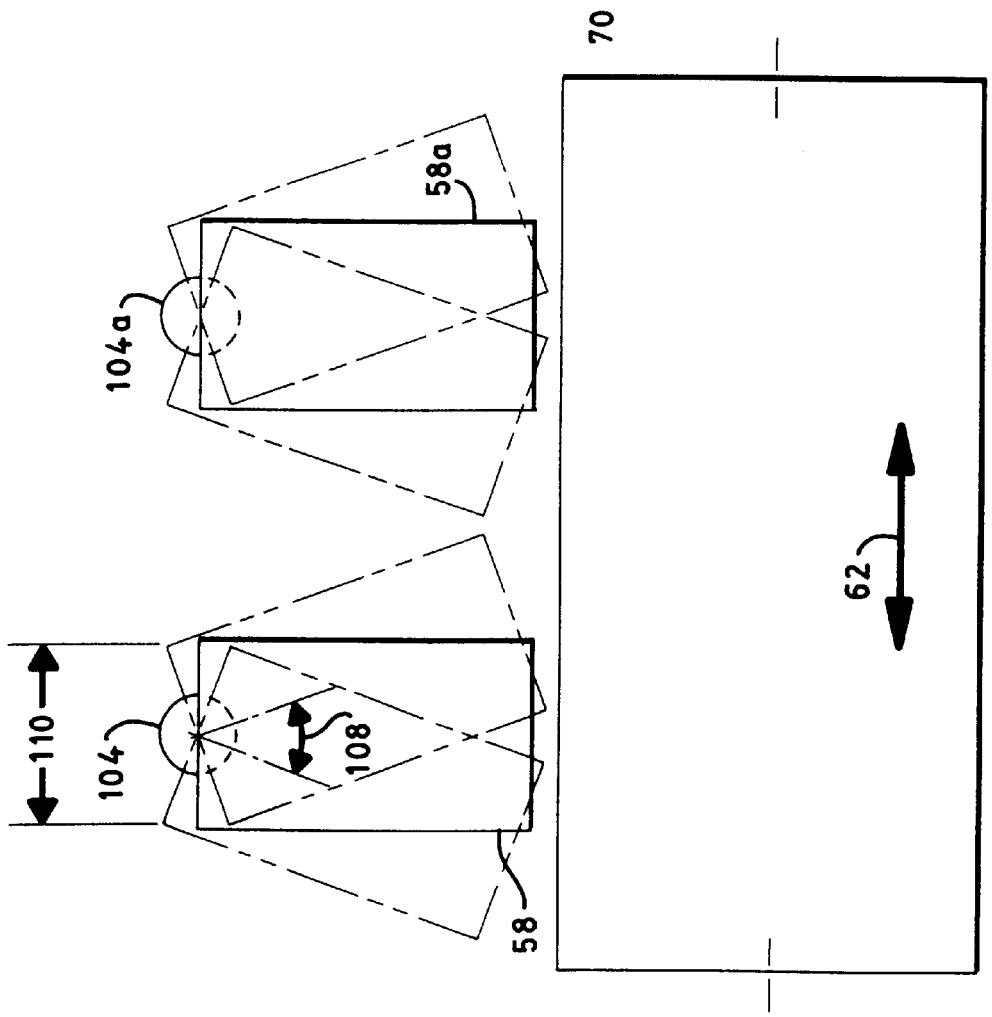
FIG. 5 representatively shows a schematic, end elevational view of the portion of the process and apparatus illustrated in FIG. 4.
Figure 6:
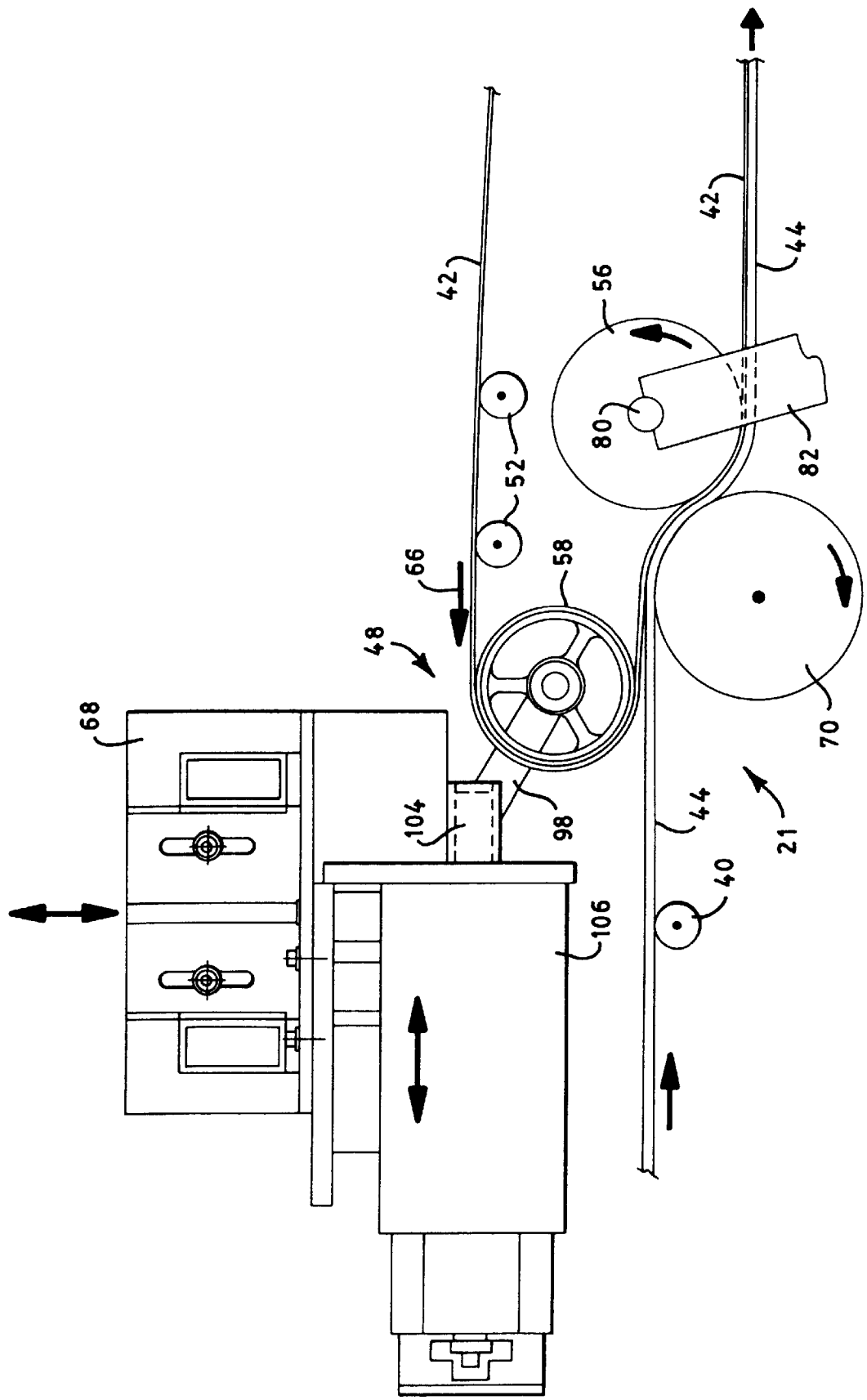
FIG. 6 representatively shows a schematic, side view of a system for adjusting the exit-span distance employed by the invention.

With reference to FIGS. 5 and 6, the oscillating of the applicator wheel 58 can operatively move at least the exit surface-region 116 of the applicator wheel 58 substantially along a cross-direction 62 of the process and apparatus. Particular aspects of the invention can include a pivot drive mechanism which selectively regulates the lateral positioning of the exit surface-region 116 of the applicator wheel 58 to operatively direct the web component 42 in the desired curved pattern on the substrate 44. In the illustrated embodiment, the applicator wheel 58 is operatively driven to continuously adjust the lateral positioning of the web component 42 in a selected periodic pattern. As a result, the web component can be applied and joined to the moving substrate 44 in a generally undulating, serpentine configuration.

Any conventional, oscillating drive system may be employed to twist the pivot shaft 104 to rock the applicator wheel 58. In particular configurations, the pivot drive system can, for example, include a cam mechanism which oscillates the pivotable arm 98 about the pivot shaft 104 through a predetermined, periodic-cycle pattern. Suitable cam mechanisms include, for example, a model 500RGH56 cam box device available from Commercial Cam Company, Inc. (CAMCO) a subsidiary of Emerson Electric Company having offices located in Wheeling, Ill. Vendors, such as CAMCO, are able to design and produce suitable cam mechanisms once they are advised of particular operational parameters. Pertinent parameters can include, for example, the dimensions and inertia of the moving components, the desired number of cycles per minute, and the particular trace pattern desired at the distal, exit surface-region 116 of the applicator wheel 58.

In other configurations the pivot drive mechanism can employ a servo mechanism, such as a pneumatic servo, a hydraulic servo, an electro-magnetic servo or the like, as well as combinations thereof. Additionally, the selected servo mechanism can be electronically controlled to regulate the desired oscillating motion. Suitable electrical servo motors include, for example, a model S-6300 ELECTRO-CRAFT servo system which is available from Electro-Craft Servo Systems, Rockwell Automation, a business having offices located in Eden Prairie, Minn. Suitable servo drive systems include, for example, a model HR 2000 RELIANCE ELECTRIC drive system which is available from Reliance Electric Motors, a business having offices located in Greenville, S.C. Suitable software for the servo system can include, for example, RELIANCE AUTOMAX software, and suitable control modules include, for example, a RELIANCE ELECTRIC 2-AXIS SERVO CONTROLLER CARD, 57C422. The software and control module are available from Reliance Electric, a business having offices located in Cleveland, Ohio.

With reference to FIGS. 2, 3 and 5, the selected pivot drive system 106 is configured to oscillate the applicator wheel 58 with a rocking motion which twists the applicator wheel around the pivot axis 102 through a selected pivot angle 108. The pivot angle may or may not be substantially symmetrically disposed with respect to a neutral line that extends through the pivot axis 102 and is aligned substantially perpendicular to the substrate web 44. The pivot angle represents the total angular arc through which the applicator wheel 58 is swept during its pivoting, rocking motion. In particular aspects, the total pivot angle 108 can be at least a minimum of about 10 degrees. The pivot angle can alternatively be at least about 20 degrees, and optionally, can be at least about 30 degrees to provide improved performance. In other aspects, the total pivot angle can be not more than a maximum of about 70 degrees. The pivot angle can alternatively be not more than about 60 degrees, and optionally, can be not more than about 50 degrees, or more, to provide improved effectiveness.

If the pivot angle is too low, the system will generate insufficient curvature in the location of the web component 42. If the pivot angle is too large, the system can produce excessive wrinkling in the web component.

In desired arrangements, the pivotable arm 98 can be configured to align its pivoting oscillation along a plane which is generally parallel with the cross-direction 62. Additionally, the plane of oscillation can be aligned generally perpendicular to the machine-direction 64.

As representatively shown in FIGS. 3 and 3A, the technique of the invention can further include the integration roll 70 which is positioned operatively adjacent the applicator wheel 58. In a particular aspect, the integration roll 70 can be positioned to provide a selected separation gap 74 between the applicator wheel 58 and the integration roll 70. The separation gap is sufficiently sized and configured to avoid interference between the applicator wheel 58 and the integration roll during the curving operation. In particular aspects, the separation gap can be at least a minimum of about 0.15 cm. The separation gap can alternatively be at least about 0.17 cm, and optionally, can be at least about 0.2 cm to provide improved performance. In other aspects, the separation gap can be not more than a maximum of about 2.6 cm. The separation gap can alternatively be not more than about 1.5 cm, and optionally, can be not more than about 0.6 cm to provide improved effectiveness.

If the separation gap is too low, there can be undesired contact between the applicator wheel 58 and other parts of the system. For example, there can be excessive contact with the integration roll. Additionally, the excessively small separation gap 74 can undesirably pinch and damage the web 42, and may undesirably rub and distort the web component.

If the separation gap is too large, the system may not be able to generate the desired amount of curvature or depth of curvature in the assembled and attached web component 42. Additionally, the system may tend to excessively wrinkle the web component during the curving process.

In addition, a selected exit-span distance 60 is provided between the applicator wheel 58 and the integration roll 70, and the exit-span distance can desirably be about 50% of a cross-directional width 46 of the web component 42. Typically, the exit-span distance is measured between the point at which the web components departs the applicator wheel 58, and the point at which the web component is joined to the substrate 44 at the surface of the integration roll 70. In desired arrangements, the exit-span distance 60 can be at least a minimum of about 15% of the cross-directional width 46 of the web component 42. The exit-span distance can alternatively be at least about 20%, and optionally, can be at least about 33% of the cross-directional width of the web component to provide improved performance. In other aspects, the exit-span distance can be not more than a maximum of about 300% of the cross-directional width 46 of the web component 42. The exit-span distance can alternatively be not more than about 75%, and optionally, can be not more than about 65% of the cross-directional width of the web component to provide improved effectiveness.

In a further aspect, the exit-span distance 60 can be at least a minimum of about 0.6 cm. The exit-span distance can alternatively be at least about 0.75 cm, and optionally, can be at least about 1.25 cm to provide improved performance. In other aspects, the exit-span distance can be not more than a maximum of about 13 cm. The exit-span distance can alternatively be not more than about 7 cm, and optionally, can be not more than about 2.5 cm to provide improved effectiveness.

If the exit-span distance is too low, excessive wrinkling can occur in the component web 42 during the curving operation. If the exit-span distance 60 is too large, however, an excessively large pivot angle 108 may be required to generate the desired amount of curvature within the web component 42.

With reference to FIG. 6, the technique of the invention can include an adjustment mechanism 68 for modifying and regulating the exit-span distance to reduce the occurrence of wrinkles in the component web 42 during the curving operation. The adjustment mechanism 68 can advantageously allow a change of the exit-span distance 60 to better match the configuration of the technique with the size of the web component 42.

The adjustment mechanism 68 can, for example, include a slotted plate with cap screw securement fasteners, "ball slide" mechanisms, jacking bolts or the like, as well as combinations thereof. Examples of "ball slide" devices include a POWERSLIDE Model 2EB12FTBG device which is available from Thomson Industries, a business having offices located in Port Washington, N.Y.

With reference to FIG. 6, the web component 42 approaches at a tangent to the integration roll 70 and contacts the moving substrate 44 that is present on the outer peripheral surface of the integration roll. The attachment contact point between the web component 42 and the moving substrate 44 is positioned upstream and prior to the location of the nip between the nip roll 56 and the integration roll 70.

In the shown configuration (e.g. FIG. 3A), the location and configuration of the nip roll 56 operatively wraps the web composite composed of the web component 42 and the assembled substrate web 44 around the circumference of the outer peripheral surface of the integration roll 70 by a selected wrap length 72. In particular aspects, the wrap length 72 can be at least a minimum of about 5% of the total circumference of the integration roll 70. The wrap length can alternatively be at least about 7% of the total circumference of the integration roll, and optionally, can be at least about 10% of the total circumference of the integration roll to provide improved performance. In other aspects, the wrap length can be not more than a maximum of about 40% of the total circumference of the integration roll 70. The wrap length can alternatively be not more than about 30% of the total circumference of the integration roll, and optionally, can be not more than about 20% of the total circumference of the integration roll to provide improved effectiveness.

If the wrap length is too low, there can be excessive interference between parts. For example, the nip roll may excessively interfere with the maintenance of the desired amount of exit-span distance 60. Additionally, the system may be less able to provide the desired amounts of curvature. For example, the excessively low wrap percentage on the applicator wheel may require the use of excessively large amounts of swinging movement of the applicator wheel to produce a desired amount of lateral, side-to-side curvature in the web component 42.

If the wrap length is too large, the system can produced excessive distortion or damage to the substrate 44. In addition, an excessively large wrap length can allow a slipping of the web component 42 and a loss of the desired amount of curvature.

The nip roll 56 is rotatable about nip roll shaft, which is aligned along the cross-direction 62 of the apparatus. The nip roll shaft 80 is mounted on a suitable support frame which holds the nip roll 56 in an operable engagement with the integration drum or roll 70 and the moving substrate 44. The support frame is constructed and arranged to resiliently urge the nip roll 56 towards the integration roll 70 with a selected level of engagement or nipping force. In addition, a support frame 82 (e.g. FIG. 6) may be constructed and arranged to selectively move the nip roll 56 away from and toward the integration roll 70 in retraction and extension operations. The ability to move the nip roll can, for example, help to facilitate maintenance.

In the illustrated embodiment, the desired levels of contact force between the nip roll 56 and the integration drum 70 can, at least in part, be provided by the weight of the nip roll 56 and its supporting system. In addition, the level of contact force and pressure between the nip roll 56 and the integration drum 70 can be augmented with other conventional mechanisms, such as pneumatic cylinders.

Having thus described the invention in rather full detail, it is readily apparent that various changes and modifications can be made without departing from the spirit of the invention. All of such changes and modifications are contemplated as being within the scope of the present invention, as defined by the subjoined claims.

We claim:

1. A process for applying a web component to a moving substrate, said process having a machine direction and comprising:
   a delivering of said web component to a rotatable applicator wheel, said applicator wheel having an entry surface-region, an exit surface-region, a transport surface-region, and an applicator wheel diameter;
   a contacting of said web component onto said entry surface-region of said applicator wheel;
   a moving of said web component along a substantially circumferential, applicator path on said transport surface-region of said applicator wheel;
   an oscillating of said applicator wheel about a pivot axis which is substantially along the machine direction of the process and spaced from said moving substrate by a pivot distance, said applicator wheel diameter being is substantially along the machine direction of the apparatus and at least about 50% of said pivot distance; and
   an applying of said web component from said exit surface-region of the applicator wheel onto said moving substrate to provide a curved web configuration.

2. A process as recited in claim 1, wherein a rotating of said applicator wheel moves said web component along said substantially circumferential, applicator path on said transport surface-region of said applicator wheel.

3. A process as recited in claim 1, further including a providing of an applicator wheel diameter which is not more than about 150% of said pivot distance.

4. A process as recited in claim 1, further including a providing of an applicator wheel diameter which is substantially equal to said pivot distance.

5. A process as recited in claim 1, further including a providing of an applicator wheel diameter which is at least about 11 cm.

6. A process as recited in claim 1, further including a securing of said web component to said moving substrate with a curved attachment.

7. A process as recited in claim 6, further including a depositing of adhesive onto said web component prior to said contacting of the web component onto said entry surface-region of said applicator wheel.

8. A process as recited in claim 6, further including a pressing of said web component onto said moving substrate.

9. A process as recited in claim 1, further including an aligning of said pivot axis substantially along a local machine-direction of said moving substrate at said applicator wheel.

10. A process as recited in claim 9, wherein said delivering of said web component moves said web component along an entry path which is substantially aligned with said pivot axis.

11. A process as recited in claim 1, wherein a rotating of said applicator wheel moves said web component from said entry surface-region to said exit surface-region of said applicator wheel.

12. A process as recited in claim 1, wherein said oscillating of said applicator wheel moves said exit surface-region of the applicator wheel substantially along a cross-direction of said process.

13. A process as recited in claim 1, wherein said delivering of said web component provides an elastomeric web component.

14. A process as recited in claim 1, further including a providing of said web component with a cross-directional width of at least about 2 cm.

15. A process as recited in claim 1, wherein a rotating of said applicator wheel moves said web component along a transport surface-region of said applicator wheel which extends along at least about 37% of a peripheral, outer circumference of said applicator wheel.

16. A process as recited in claim 1, further including
   a positioning of an integration roll operatively adjacent said applicator wheel, and
   a providing of an exit-span distance between said applicator wheel and said integration roll, wherein said exit-span distance is at least about 15% of a cross-directional width of said web component.

17. A process as recited in claim 16, wherein said providing of said exit-span distance employs an exit-span distance of not more than about 300% of the cross-directional width of said web component.

18. A process as recited in claim 16, wherein said providing of said exit-span distance employs an exit-span distance of at least about 0.75 cm.

19. A process as recited in claim 16, wherein said providing of said exit-span distance employs an exit-span distance of not more than about 13 cm.

20. A process as recited in claim 1, further including a positioning of an integration roll operatively adjacent said applicator wheel; and a providing of a separation gap of at least about 0.15 cm between said applicator wheel and said integration roll.

21. A process as recited in claim 20, wherein said providing of said separation gap employs a separation gap of not more than about 2.6 cm.

22. A process as recited in claim 1, wherein said oscillating of said applicator wheel employs a cam mechanism.

23. A process as recited in claim 1, wherein said oscillating of said applicator wheel employs a servo mechanism.

24. A process as recited in claim 1, wherein said oscillating of said applicator wheel employs an electronically controlled servo mechanism.

25. An apparatus for applying a web component to a moving substrate, said apparatus having a machine direction and comprising:
   a rotatable applicator wheel having an entry surface-region, an exit surface-region, a transport surface-region and an applicator wheel diameter, said applicator wheel configured to move said web component along a substantially circumferential, applicator path with said transport surface-region of said applicator wheel;
   a web conveyor which delivers said web component to said applicator wheel and contacts said web component onto said entry surface-region of said applicator wheel; and
   a pivot drive mechanism which oscillates said applicator wheel about a pivot axis to direct said web component from said exit surface-region of the applicator wheel onto said moving substrate in a curved web configuration, wherein said pivot axis is spaced from said moving substrate by a pivot distance, and said applicator wheel diameter is at least about 50% of said pivot distance.

26. A process for applying a web component to a moving substrate, said process having a machine direction and said process comprising:
- a delivering of said web component to a rotatable applicator wheel, said applicator wheel having an entry surface-region, an exit surface-region, a transport surface-region, and an applicator wheel diameter;
- a contacting of said web component onto said entry surface-region of said applicator wheel;
- a moving of said web component along a substantially circumferential, applicator path on said transport surface-region of said applicator wheel;
- an oscillating of said applicator wheel about a pivot axis which is substantially along the machine direction of the process and spaced from said moving substrate by a pivot distance, said applicator wheel diameter being is at least about 50% of said pivot distance;
- an applying of said web component from said exit surface-region of the applicator wheel onto said moving substrate to provide a curved web configuration;
- a positioning of an integration roll operatively adjacent said applicator wheel;
- a positioning of a pressing nip roll downstream from said applicator wheel;
- a directing of said moving substrate with said integration roll into an operative contact with said web component;
- an urging of said web component against said substrate in a nip between said applicator wheel and said pressing nip roll; and
- a wrapping of said moving substrate and web component around said integration roll along a wrap length which is at least about 5% of a total circumference of said integration roll.

27. A process as recited in claim 26, wherein said wrapping of said moving substrate and web component around said integration roll is conducted by employing said pressing nip roll.

28. An apparatus for applying a web component to a moving substrate, said apparatus having a machine direction and comprising:
- a rotatable applicator wheel having an entry surface-region, an exit surface-region, a transport surface-region and an applicator wheel diameter, said applicator wheel configured to move said web component along a substantially circumferential, applicator path with said transport surface-region of said applicator wheel;
- a web conveyor which delivers said web component to said applicator wheel and contacts said web component onto said entry surface-region of said applicator wheel;
- a pivot drive mechanism which oscillates said applicator wheel about a pivot axis to direct said web component from said exit surface-region of the applicator wheel onto said moving substrate in a curved web configuration, wherein said pivot axis is substantially along the machine direction of the apparatus and spaced from said moving substrate by a pivot distance, and said applicator wheel diameter is at least about 50% of said pivot distance;
- an integration roll which is positioned operatively adjacent said applicator wheel; and
- a pressing nip roll which is positioned downstream from said applicator wheel;

wherein
- said integration roll is configured to direct said moving substrate into contact with said web component;
- said pressing nip roll is positioned downstream from said applicator wheel and is configured to urge said web component against said substrate in a nip between said applicator wheel and said pressing nip roll; and
- said pressing nip roll is configured to wrap said moving substrate and web component around said integration roll along a circumferential wrap length which is at least about 5% of a total circumference of said integration roll.

* * * * *